United States Patent [19]
Rao

[11] Patent Number: 5,475,120
[45] Date of Patent: Dec. 12, 1995

[54] METHOD FOR THE ISOLATION AND PURIFICATION OF TAXOL AND ITS NATURAL ANALOGUES

[75] Inventor: Koppaka V. Rao, Gainesville, Fla.

[73] Assignee: University of Florida, Gainesville, Fla.

[21] Appl. No.: 333,382

[22] Filed: Nov. 2, 1994

Related U.S. Application Data

[63] Continuation-in-part of Ser. No. 915,736, Jul. 16, 1992, Pat. No. 5,380,916, which is a continuation-in-part of Ser. No. 611,109, Nov. 2, 1990, abandoned.

[51] Int. Cl.$^6$ .................. C07D 305/14; A01N 43/20
[52] U.S. Cl. .................. 549/510; 210/656; 560/107
[58] Field of Search .................. 549/510; 514/449; 210/656; 560/107

[56] References Cited

U.S. PATENT DOCUMENTS

| | | | |
|---|---|---|---|
| 4,814,470 | 3/1989 | Colin et al. | 514/449 |
| 4,924,011 | 5/1990 | Denis et al. | 549/510 |
| 4,960,790 | 10/1990 | Stella et al. | 514/449 |
| 5,019,504 | 5/1991 | Christen et al. | 435/123 |
| 5,250,722 | 10/1993 | Bombardelli et al. | 560/104 |
| 5,254,580 | 10/1993 | Chen et al. | 514/449 |
| 5,279,949 | 1/1994 | Nair | 435/123 |
| 5,364,947 | 11/1994 | Murray et al. | 549/510 |

OTHER PUBLICATIONS

Huang, C. H. O. et al. (1986) "New Taxanes from *Taux Brevifolia*, 2" Journal of Natural Products 49(4):665–669.
McLaughlin, J. L. et al. (1981) "19–Hydroxybaccatin III, 10–Deacetylcephalomannine, and 10–Deacetyltaxol: New Antitumor Taxanes from *Taxus Wallichiana*" Journal of Natural Products 44(3):312–319.
Senilh, V. et al. (1984) "Mise en Evidence de Nouveaux Analogues du Taxol Extraits de *Taxus Baccata*" Journal of Natural Products 47(1):131–137 (Abstract only).
Wani, M. C. et al. (1971) "Plant Antitumor Agents. VI. The Isolation and Structure of Taxol, a Novel Antileukemic and Antitumor Agent from *Taxus brevifolia*" Journal of the American Chemical Society 93(9):2325–2327.
Witherup, K. M. et al. (1989) "High Performance Liquid Chromatographic Separation of Taxol and Related Compounds from *Taxus Brevifolia*" Journal of Liquid Chromatography 12(11):2117–2132.
Miller, R. W. et al. (1981) "Antileukemic Alkaloids from *Taxus wallichiana* Zucc." J. Org. Chem. 46(7):1469–1474.
Kingston, D. G. I. et al. (1982) "New Taxanes from *Taxus Brevifolia*" Journal of Natural Products 45(4);466–470.
Castor, T. P., T. A. Tyler (1993) "Determination of Taxol in *Taxus media* Needles in the Presence of Interfering Components" Journal of Liquid Chromatography 16(3):723–731.
Chmurny, G. N. et al. (1993) "NMR Structure Determination and Intramolecular Transesterification of Four Diacetyl Taxinines Which Co–Elute with Taxol Obtained from *Taxus x. Media* HicksII Needles" Phytochemistry 34(2):477–483.

*Primary Examiner*—Richard L. Raymond
*Assistant Examiner*—Deborah Lambkin
*Attorney, Agent, or Firm*—Saliwanchik & Saliwanchik

[57] ABSTRACT

An improved method for isolating taxol and certain clinically important analogues of taxol from a crude extract of a naturally occuring Taxus species comprising treating the extract by reverse phase liquid chromatography on an adsorbent, causing the taxol and the taxol analogues to be absorbed on the adsorbent, and recovering taxol and the natural analogues of taxol from the adsorbent by elution with an elutant. The compounds thus isolated in pure form are taxol, taxol-7- xyloside, 10-deacetyltaxol, 10-deacetyltaxol-7-xyloside, cephalomannine, cephalomannine-7-xyloside, 10-deacetylcephalomannine-7-xyloside, baccatin III, 10-deacetylbaccatin III, baccatin VI, brevitaxane A, and taxiflorine.

22 Claims, 5 Drawing Sheets

METHOD FOR THE ISOLATION AND PURIFICATION OF TAXOL AND ITS NATURAL ANALOGUES

CROSS-REFERENCE TO RELATED APPLICATIONS

This application is a continuation-in-part of application Ser. No. 07/915,736, filed Jul. 16, 1992; now U.S. Pat. No. 5,380,916 which is a continuation-in-part of application Ser. No. 07/611,109, filed Nov. 2, 1990, now abandoned.

BACKGROUND OF THE INVENTION

1. Field of the Invention

This invention relates to the isolation and purification of taxol and its natural analogues from a naturally occurring Taxus species or cell cultures thereof and, more particularly, to an improved method for isolating taxol and the congeners thereof from the Taxus species by reverse phase liquid chromatography.

2. Related Art

Taxol was first isolated in 1971 from the western yew, *Taxus brevifolia* by Wani et al. (1971), who characterized, its structure by chemical and X-Ray crystallographic methods.

Taxol is a member of the taxane family of diterpenes having the following structure:

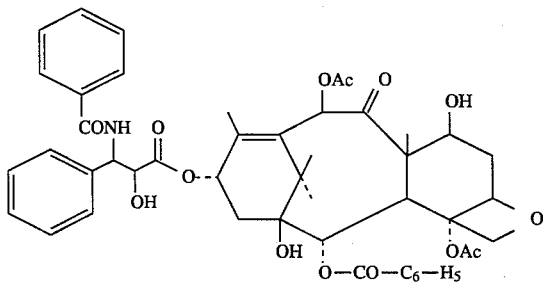

Taxol and various taxane analogues or derivatives, including cephalomannine, are highly cytotoxic and possess strong in vivo activities in a number of leukemic and tumor systems. Especially, taxol is considered an exceptionally promising cancer chemotherapeutic agent. On the basis of its novel mode of action and activity shown in clinical trials, taxol was approved by the FDA for treatment of ovarian carcinoma. In view of the activity shown by taxol on other tumors such as breast and lung tumors, regulatory approval for the use of taxol in the treatment of these tumors is also currently under study. However, the major problem with the production of pharmaceuticals which incorporate taxol as an ingredient for treatments is the limited availability of the compound. One idea that has been thoroughly impressed on the minds of taxol scientists as well as on the lay public is that taxol is a very scarce commodity because the bark of the Pacific yew yields less than 0.01%.

A primary natural source for taxol is several species of very slow-growing yew (genus Taxus, family Taxaceae). The currently practiced procedures for isolating taxol from bark have the disadvantages of being fatal to the source, being very difficult to carry out, and producing low yields. For example, C.H.O. Huang et al. (1986) reported a 0.01% yield from a large scale isolation starting with 806 lbs. or more of *Taxus brevifolia* bark. Similar procedures have been reported which comparably produce low yields, ranging from as low as 0.004%, up to about (but not above) 0.017%. A yield of 0.01% translates into 1 g being isolated from 10 kg of the bark, or 1 kg of taxol from 10,000 kg (≈22,000 lbs) of the bark. A mature tree is said to yield 20–25 lbs. of the bark, and this means that nearly 800–1000 trees are needed to produce a kilogram of taxol. Accordingly, use of the bark is being rapidly phased out as the primary source of taxol.

Senilh and co-workers studied the bark of the European yew (*Taxus baccata*) and described the isolation of a large number of compounds: taxol (or taxol A) (0.0165%), cephalomannine (or taxol B), 0.0064%), and others. The procedure used by Senilh and co-workers also includes multiple (seven) steps for the isolation of taxol, also primarily employing normal phase chromatography columns for the separation procedures.

(1) Extraction with alcohol and concentration.
(2) Partition between water and dichloromethane.
(3) "Filtration chromatography."
(4) Silica column chromatography.
(5) Alumina chromatography.
(6) Medium pressure silica column chromatography.
(7) Preparative HPLC.

For the other analogues, two or three other chromatographic columns, followed by preperative HPLC, were used.

Other schemes for the large-scale production of taxol from T. brevifolia bark have also been developed. One such method used by Polysciences, Inc. includes the following steps:

(1) The dried ground bark was extracted with methanol or ethanol and the combined extract concentrated to remove most of the alcohol.
(2) The concentrate was then extracted with dichloromethane and the solvent extract concentrated to a powder.
(3) This powder was stirred with a mixture of acetone and ligroin (1:1) and filtered to remove the insoluble matter.
(4) The filtrate which contained taxol was concentrated, dissolved in 30% acetone in ligroin, and applied to a column of Florisil.
(5) The taxol fraction from the column was purified by crystallization twice.
(6) The crystalline taxol was further subjected to chromatography on a silica column. In this step, the closely related analogue, cephalomannine, was separated from taxol.
(7) The purified taxol obtained from the column was crystallized twice.
(8) Unseparated mixtures and mother liquors were recycled through the silica column to obtain additional amounts of pure taxol.

The yield of taxol in this process was reported as 0.004–0.01% based on the bark used. The isolation was described by other workers: Miller et al., 1981; McLaughlin et al., 1981; Kingston et al., 1982; and Senihl et al., 1984. The reported yields of taxol from various species of yew range from 50 mg/kg to 165 mg/kg (i.e., 0.005–0.017%). At present, the bark of *Taxus brevifolia* is still being used as the major source of taxol.

Because of (a) the rather low (0.01% or less) yields of taxol from the bark, (b) the relative unavailability of any other useful analogues, and (c) the need to cut the slow-growing trees to harvest the bark, it was decided that the bark was not an attractive source for taxol. Therefore, besides isolation from the bark, there are currently three avenues that are being pursued for the future production of taxol: (1) isolation from renewable plant parts, e.g., the ornamental yew clippings and needles; (2) semi-synthesis of taxol; and (3) production of taxol by tissue culture procedures.

Laboratory scale isolations of taxol and its analogues from different parts of different species of Taxus have been described. Miller and co-workers (see Miller et al. [1981], supra), working with the roots, stems, and leaves of *Taxus wallichiana*, isolated taxol (0.01%), an analogue called cephalomannine (0.016%), among other now-commonly known analogues. The Miller procedure consists of eight steps, including two normal phase chromatography steps.

(1) Extraction of the plant and concentration of the extract to a solid.

(2) Defatting by partition between water and hexane.

(3) Extraction with chloroform and concentration.

(4) Silica column chromatography.

(5) A second silica column chromatography.

(6) Countercurrent distribution.

(7) A second countercurrent distribution.

(8) Preparative HPLC.

Kingston and co-workers (Kingston, et al, 1982), working with taxol-free fractions obtained from the large-scale processing of the bark of *Taxus brevifolia*, isolated very minute yields (<0.0003%) of these analogues, which reinforce the notion that the yield of taxol from T. brevifolia is very low and that few, if any, useful analogues can be obtained. From the needles of *Taxus baccata*, Colin et al. isolated 10-deacetyl baccatin III, which they used to synthesize a number of derivatives of taxol. See U.S. Pat. No. 4,814,470.

The use of the tissue from the ornamental yew (*Taxus x media* Hicksii) for isolating taxol and taxanes has been described in U.S. Pat. No. 5,279,949. The process described in the '949 patent, however, involves column chromatography using normal phase silica. Specifically, the '949 patent describes a separation procedure as follows:

(1) the fresh needles were extracted with 70% alcohol;

(2) the extract was decolorized with charcoal and filtered;

(3) the extract was concentrated to remove most of the organic solvent;

(4) the aqueous concentrate was centrifuged to separate the precipitated solid (containing taxol);

(5) the solid was then subjected to normal phase silica chromatography;

(6) a second, low pressure silica column was run on the crude taxol fraction; and (7) a reverse phase column was used for final purification. Alternatively, instead of step (4), the aqueous concentrate was extracted with ethyl acetate, the extract concentrated, and applied to the silica column (step 5). By contrast, our process using a reverse phase column process which has particular advantages over normal phase chromatography, works well with the extract from the needles of this yew, even on a pilot plant scale.

Upon the discovery of *Taxus x media* Hicksii needles as a taxol source, Witherup et al., 1990 showed that the needles contain as much taxol as the bark, i.e., about 0.01%, and isolated taxol by an unspecified method in a yield of 0.006%. This plant produces several unrelated taxanes which follow taxol in the purification step (whether using the normal phase or reverse phase column method) and their complete removal from taxol (to meet the FDA specifications) will require at least two (or more) columns besides the initial column. Unlike the situation with cephalomannine, which is present only to a minor extent when taxol is isolated from bark, the taxanes that accompany taxol isolated from the needles of the ornamental yew are present in much higher concentrations than taxol.

The published literature on this subject generally consists of methods using analytical HPLC of the needles (and other parts of the plants) and listing the yields based on these analyses. It is also clear from some of the papers that the needles contain, besides taxol, some unrelated taxaries (cinnamate esters with a 4/20 double bond instead of the oxetane ring) which co-elute with taxol in the analytical HPLC (Castor and Taylor, 1993). Two of these compounds were isolated in impure form and characterized spectrally (Chmurny et al., 1993).

Also, in view of the high therapeutic potential of taxol, the synthesis of the compound has attracted much interest among synthetic chemists worldwide. Although methods for total synthesis of taxol have been announced by at least two groups of researchers, development of a practical process is likely to be several years away. The semi-synthesis procedure involves conversion of a taxol precursor to taxol through a series of several chemical conversion steps. The European yew, *Taxus baccata*, is being cultivated on a large scale for the isolation of 10-deacetyl baccatin III from its needles, so that tiffs compound can be converted into taxol through semisynthesis.

The yield of 10-deacetyl baccatin III from the needles of *T. baccata* is variably reported from 0.02–0.1%, with an average of 0.05 %. It appears that neither taxol nor any of the other analogues are being isolated from this source. In addition, the semisynthetic conversion is said to involve seven steps and, under the best of circumstances (90% yield at each step), an overall yield of 40% may be expected. This translates into a relatively low yield of approximately 0.02% from the plant source.

The subject process can be applied to the isolation of 10-deacetyl baccatin III, as well as taxol and other analogues, from the needles of *T. baccata*.

Much progress has been made over the past few years to grow the Taxus callus tissue under cell culture conditions to produce taxol. It is widely assumed that this method may replace others that are based on conventional plant extraction, etc. Indications are that the culture produces not only taxol, but also cephalomannine and some of the xylosides. Therefore, a simple, inexpensive purification procedure will still be necessary if such tissue culture methods are ultimately developed for wide-scale use.

Because of the current state of available synthesis procedures, and other alternative methods for purifying or obtaining the valuable taxol compound, the isolation of taxol from Taxus species, despite low yields, will be the only reliable supply source for clinical quantities of taxol for years to come. Unfortunately, the currently available isolation methods require multiple steps, which translates into increased time and expense while still producing relatively low yields. Thus, simplified purification techniques which provide higher yields of taxol are needed to provide greater quantities of this promising therapeutic agent at reduced cost. The present invention provides a purification technique which accomplishes this goal.

BRIEF SUMMARY OF THE INVENTION

In view of the foregoing, it is a primary objective of this invention to provide an improved method for the isolation of taxol and its natural analogs from a Taxus species.

It has now surprisingly been found that taxol and the congeners thereof can be isolated and purified from *Taxus brevifolia* and other Taxus species in high yields by a single reverse phase liquid chromatography column. By the subject method, at least seven other natural analogues of taxol, including 10-deacetyltaxol-7-xyloside, taxol-7-xyloside, 10-deacetylbaccatin III, and 10-deacetyltaxol can also be obtained by direct crystallization. Some of these analogues can be convened to taxol by chemical synthesis.

According to this invention, there is provided a method for isolating taxol and natural analogues of taxol from the crude extract of a naturally occurring Taxus species comprising the steps of:

(a) treating the crude extract comprising taxol and its natural analogues by reverse phase liquid chromatography using a preparative scale column containing an adsorbent and causing the taxol and the natural analogues to be adsorbed on the adsorbent;

(b) eluting the taxol and the natural analogues of taxol from the adsorbent; and (c) recovering the taxol and the natural analogues in separate fractions of the eluate.

Novel analogues of taxol have also been isolated and described.

These and other objectives, as well as the nature, scope, and utilization of this invention, will become readily apparent to those skilled in the art from the following description, the drawings, and the appended claims.

DETAILED DISCLOSURE OF THE INVENTION

Taxol and its natural analogues isolated and purified in accordance with this invention are characterized by the following chemical structure:

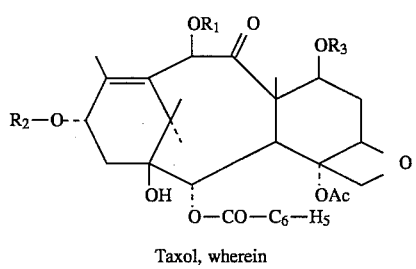

Taxol, wherein

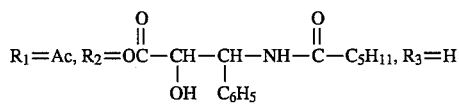

-continued

Tazxol C, wherein

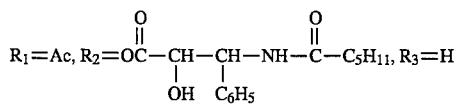

10-deacetyltaxol C, wherein

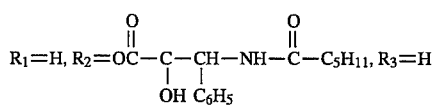

10-deacetyltaxol C-7-xyloside, wherein

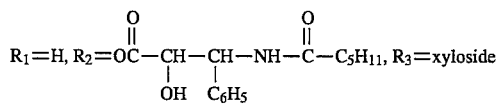

Tacxol-7-xyloside, wherein

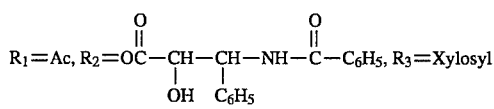

10-deacetyltaxol-7-xyloside, wherein

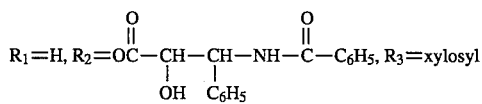

Cephalomannine, wherein

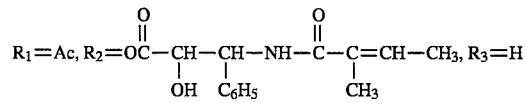

Cephalomannine-7-xyloside, wherein $R_1 = Ac$,

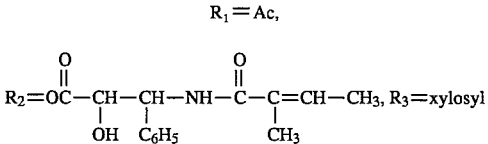

10-deacetylcephalomannine-7-xyloside, wherein $R_1 = H$,

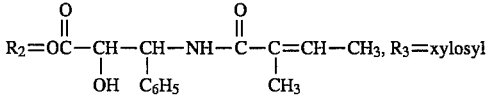

Baccatin III, wherein $R_1$=AC,$R_2$=H,$R_3$=H 10-deacetylbaccatin III, wherein $R_1$=H,$R_2$=H,$R_3$=H Baccatin VI, which has the structure:

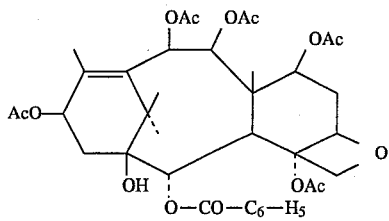

Brevitaxane A (also called brevifoliol), which has the structure:

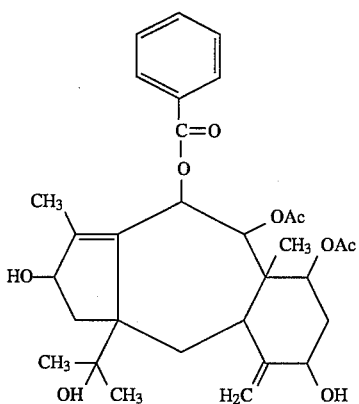

Taxiflorine, which is a novel compound isolated from *Taxus floridana*, has the structure

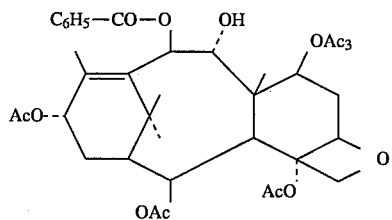

which is shown as having an acetyl group at the 7 position and an OH at the 9 position. A second isomer for this compound has also been discovered wherein the acetyl group is at the 9 position and the OH is at the 7 position. These isomers are isolated as a mixture as determined by the formation of two different peaks in the spectral analysis. Acetylation of either isomer yields acetyl groups on both the 7 and 9 positions. NMR spectral data were determined for the acetate.

The starting material for this invention is a plant material selected from the group of plants commonly referred to as taxads. The most suitable plants of this group are species of Taxus. Among Taxus species, *Taxus brevifolia* is particularly preferred. Also, a preferred plant source is *Taxus floridana*. While it is convenient to use certain parts of the Taxus tree in this invention, taxol and its natural analogues can be extracted from the whole plant or from separated parts such as wood, stems, roots, leaves (needles), seeds, or mixtures thereof. The material to be extracted can be either fresh or dried. Preferably, the bark or the needles are used. Further, the method of this invention can be used to purify taxol or its natural analogues from plant cells grown, or culture supernatants obtained by using in vitro culture technology. Additionally, the method is applicable to the separation and purification of taxol and taxol analogues from mixtures treated by conventional chromatographic techniques. The method can be further applied to the separation and purification of taxol and its analogues obtained from the semi-synthesis or total synthesis procedures.

Figure 1:
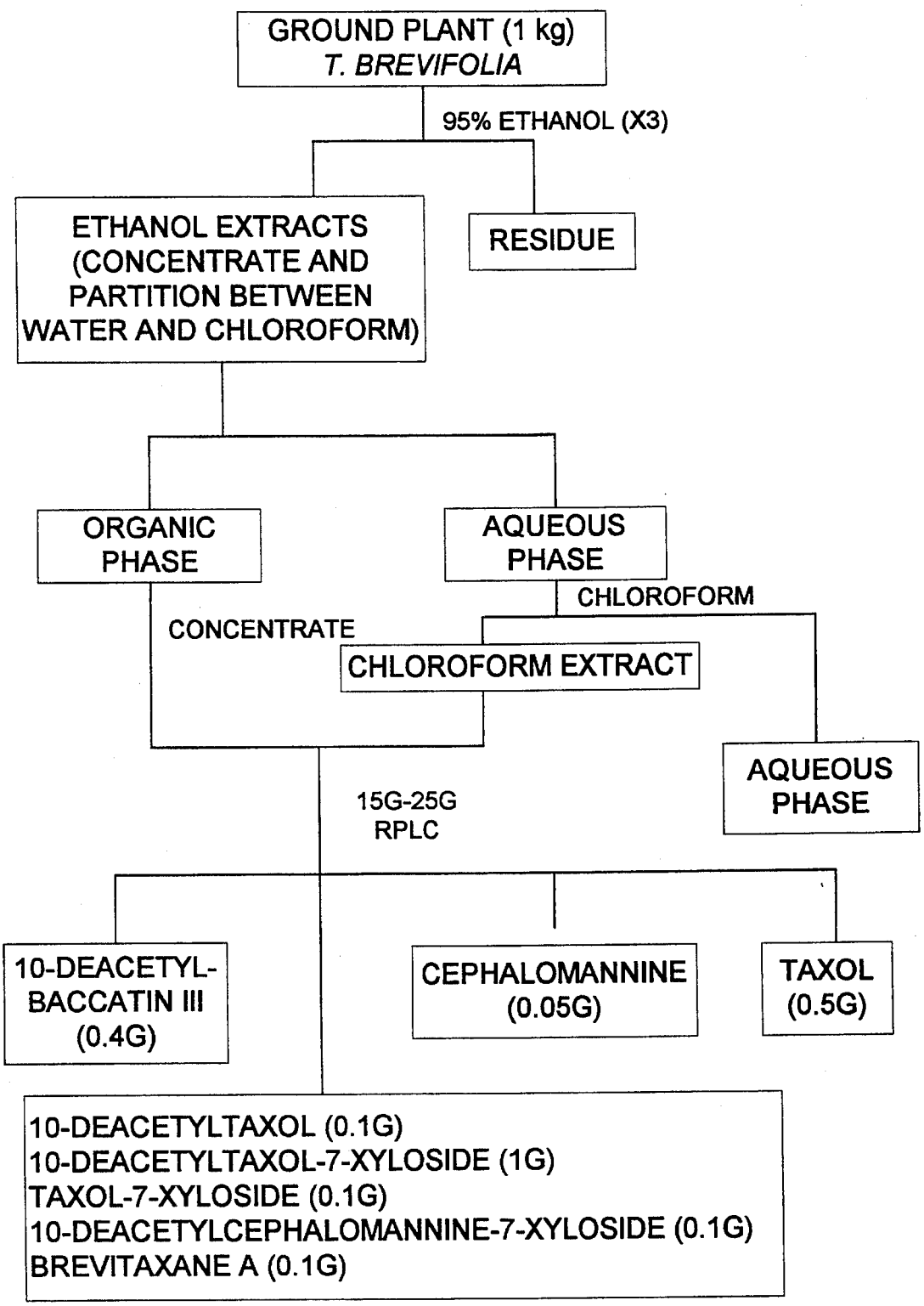
FIG. 1 shows a separation scheme for isolating taxanes from *Taxus brevifolia* in accordance with this invention.

In one embodiment of the subject process, the material is first air-dried at ambient temperature and ground to a suitable particle size usually ranging from about 0.001 to about 10 $mm^3$. This may be accomplished by serial passage through a chipper and a conventional grinding mill. The ground material is then extracted with a polar solvent such as an alcohol, preferably 95% ethanol or methanol. The extraction normally continues to 24 hours at ambient temperature. The solvent material is concentrated at reduced pressure to approximately 5–10% of its original volume. The concentrated extract of the ground plant material (0.1 g to 1 kg) is processed in a solvent-partitioning scheme, such as shown in FIG. 1, in FIG. 2, or in FIG. 3.

The concentrate is thus partitioned between two immiscible solvents, preferably a water-chloro, form or water-dichloromethane mixture. Other representative solvents suitable for the partition process include 1,2-dichloroethane, 1,1-dichloromethane, 1,1-dichloroethane, benzene, toluene, methyl isobutyl ketone, and amyl acetate. After equilibration, the organic phase is separated and the aqueous phase is extracted with the organic solvent for several times. The combined organic phase is concentrated at reduced pressure to dryness. Although other known processes also use an extraction step, it is noted that the subject process does not necessarily require a defatting step to remove the fats and waxes.

The mass obtained constitutes a crude taxane extract substantially free from the extraction solvent. Different forms of the crude extract result, such as a solid, syrup, or a gummy semisolid, depending on the extraction conditions used. The term "crude taxane extract" used herein means an extract which has not substantially been purified by conventional column chromatographic techniques or any other equivalent purification methods.

In accordance with this invention, the crude taxane extract is subjected to reverse phase liquid chromatography ("RPLC") in order to separate taxol and the natural analogues of taxol contained in the extract and to isolate each compound in pure form. Several variables are usually examined to achieve separation and purification by liquid chromatography: column packing (stationary phase or adsorbent), composition of an eluant (mobile phase), column dimension, and eluant flow rate.

When practicing this invention, silica gel based reverse phase particles are particularly suitable as the adsorbent. Preferably, hydrocarbon-bonded silica gel having $C_8$ to $C_{18}$ alkyl groups, cyano-bonded silica gel, or phenylalkyl-bonded silica gel is used. Especially preferred is $C_{18}$ bonded silica gel.

A noteworthy feature of this invention is the preferred use of a single column in chromatography. This single column technique accomplishes the separation of taxol and its natural analogues from the crude extract, affording crystalline solids from which purified taxanes are obtained by recrystallization. Such efficient separation by a single column is totally unexpected and is contrary to the belief of those skilled in the art that the taxol separation process always requires a multicolumn system.

Solvents (elutants) useful in this invention can be selected by reference to the standard practices of chromatography. A polar eluant, such as lower alcohol, acetone, acetic acid, and acetonitrile, is usually employed when the adsorbent has low polarity. A water-miscible organic solvent, such as acetonitrile or methanol, in water is preferably used as the eluant. An acetonitrile-water mixture with acetonitrile being in the range of 0% to 100% is conveniently employed.

The concentration limits of the gradients are determined by the concentration of organic solvent necessary to elute taxanes from the adsorbent and the requirement that the organic solvent be completely miscible and exist in a single phase at the concentration required to elute the taxaries. Initially, a concentration of 10–40% acetonitrile is used and is increased as separation and purification progresses. Other solvents with broad water-miscibility properties similar to those of acetonitrile are also suitable, e.g., straight or branched chain alkanols containing from 2 to 6 carbons including, but not limited to, ethanol, n-propanol, isopropanol, n-butanol, and hexanol. Lower aliphatic ketones such as acetone, methyl ethyl ketone, and diethyl ketone; cyclic esters such as tetrahydrofuran and dioxane; dimethyl formamide; esters such as methyl and ethyl acetates; and dimethyl sulfoxide can also be used without adverse effects on separation. These solvents and others are used alone or in combination with acetonitrile.

The chromatographic column dimensions, and the temperature, flow rates, and time of chromatographic separations are not critical to the practice of this invention, and are based primarily upon the requirements for efficient chromatography which are known to those of skill in the art or can be readily determined without undue experimentation.

The liquid chromatography systems of this invention are preferentially used in a preparative mode (greater than 100 mg quantities). Preparative columns require larger load capacity than analytical columns and typically are 13–150 mm O.D.×300–1800 mm long. Those skilled in the art of chromatography can, without undue experimentation, select chromatography bed dimensions (i.e., the particle size of an adsorbent material) appropriate to the amounts of material being separated. Flow rates of eluant are adjusted based on such factors as the column dimensions, the degree of peak resolution desired; the particle size of the stationary phase, and the time required to achieve satisfactory peak resolution. For example, preparative columns typically use flow rates from 10 ml to several hundred ml/minute. By contrast, analytical scale chromatography columns are much smaller, allowing smaller load capacity, and require the use of slower flow rates.

The times required for chromatographic runs range from about 10 minutes to about 30 hours. Temperatures for chromatographic separation are typically at ambient temperature, although slightly higher temperatures can be used.

When practicing the chromatographic separation according to this invention, either a high pressure liquid chromatography (HPLC) mode, which operates at high pressures (500–2000 p.s.i.), or medium or low pressure liquid chromatography (MPLC or LPLC, respectively) modes, which generally operate at pressures from 10–500 p.s.i., can be used.

Having described specific chromatographic techniques and conditions suitable for this invention, a preferred embodiment of the isolation, separation, and purification of the taxane derivatives in accordance with this invention is described below.

The subject process was devised to reduce the number of steps and thereby make it simpler, and, at the same time, increase the yields. It is applicable to all pans of the plant without any changes. In the description of the invention, the basic steps such as the extraction, partition, and chromatography are the same. Since different plant materials such as the bark, needles, etc., contain different constituents, the last step which deals with the purification of these constituents can be modified, according to procedures well known in the art, in order to obtain optimal yields of the desired compounds. The process consists of the following steps:

The crude solvent extract which comprises taxol and the natural analogues of taxol is subjected to reverse phase column chromatography using the separation conditions as set forth above. This procedure, which uses increasing concentrations of acetonitrile in water as a mobile phase, results in a series of fractions which contain taxol and related analogues eluted in the order of decreasing polarity. These compounds (in their order of elution) are (1) 10-deacetylbaccatin III; (2) 10-deacetylcephalomannine-7-xyloside; (3) brevitaxane A; (4) 10-deacetyltaxol-7-xyloside; (5) 10-aleacetyl taxol C-7-xyloside; (6) taxol-7-xyloside; (7) 10-deacetyltaxol;(8) cephalomannine; and (9) taxol. All these analogues crystallize out directly from the eluted fractions. The crude crystals of taxol and the above taxol analogues (except brevitaxane A, which crystallizes out with 10-deacetylcephalomannine-7-xyloside) can conveniently be recrystallized. Recrystallization may be carried out by standard techniques known in the art. Although a variety of common organic solvents can be used, a water miscible solvent in water, such as methanol/water or acetonitrile/water, is preferred. Other representative solvents include chloroform, benzene, ethyl acetate, ether, and acetone. These solvents are normally used in combination with a nonpolar solvent such as ligroin or ni-pentane. The mother liquors from the recrystallization are combined with fractions less rich in taxol, and are subjected to chromatography again using the same separation conditions as those used for the first separation. Likewise, other taxanes can be chromatographically processed. An adsorbent different from that used for the first separation may be employed in RPLC. After recrystallization, a combined yield of taxol is obtained. Similarly, cephalomannine is isolated and purified by recrystallization.

The more polar fractions may likewise be chromatographed to separate 10deacetylbaccatin III, although the compound either crystallizes out directly from the fractions or can be crystallized upon concentration of the fractions. Alternatively, this second chromatography on the reverse stationary phase can be substituted by standard chromatography using a normal phase silica gel column or a Florisil column or even an alumina column. The taxol analogues can be recrystallized from the same solvent combinations as set forth above, affording pure natural products. In a similar manner, other compounds like 10-deacetylcephalomannine-7-xyloside; 10-deacetyltaxol-7-xyloside; and 10-deacetyl taxol C-7-xyloside can be purified by recrystallization of these crystals.

In accordance with another alternative embodiment of this invention, the concentrated extract of the needles (fresh or dried) of the Taxus plant is processed in a slightly different manner from that used for the bark extract. The needle extract can be partitioned between aqueous methanol and ligroin to remove lipid components including chlorophylls, carotenoids, oils, and the like. It is noted that the subject invention does not require this defatting step. However, if desired, the defatting step can be included and, advantageously, does not interfere with the isolation process. The aqueous methanol phase is extracted successively using suitable organic solvents with different polarities. The less polar extract mainly contains taxol, and the more polar extract contains 10-deacetylbaccatin III, with brevitaxane A in both extracts. Both extracts are separately subjected to RPLC using substantially the same separation conditions as those described previously. Early fractions from the two separations are combined and concentrated to yield 10deacetylbaccatin III. Later fractions are combined and concentrated to yield brevitaxane A, cephalomannine, and taxol. After fractional separation, all the taxol analogues can be isolated and recrystallized. For an additional chromatography (rechromatography), a silica gel column or a Florisil column or an alumina column may be employed in lieu of a reverse phase column, if desired. Alternatively, the aqueous methanol phase after the ligroin partition is extracted with a single solvent such as chloroform. The taxane extract is then chromatographed on a reverse phase column to separate 10-deacetylbaccatin III, brevitaxane A, cephalomannine, and taxol, respectively, from each other. Each taxane can be isolated and recrystallized as previously described.

Alternatively, a needle methanol extract in concentrated form is partitioned between water and chloroform. The chloroform phase, after concentration, is dissolved in methanol/acetone, and can be passed through a RPLC column in order to remove the lipid components which remain on the column, while taxol and the natural analogues of taxol are eluted from the column. This precolumn treatment obviates the need for the above-indicated partition using ligroin, and provides for a simple and more convenient alternative to the ligroin treatment. The eluate is concentrated and can be chromatographed on a RPLC column as a suspension, e.g., in 20–30% acetonitrile/water.

If the needles of *Taxus fioridana* are extracted and processed as described above, 10-deacetylbaccatin III, baccatin VI, and taxol result. The needles of *Taxus fioridana* appear to be superior to the *Taxus brevifolia* as a Taxus source in terms of the isolated yields of taxanes.

Interestingly, 10-deacetylbaccatin III is found in the leaves of Taxus baccata L. and can be extracted in fairly high yields (0.03% yield is reported in Jean-Noel Denis et al., 1988). Denis et al., ibid, describe the synthesis of taxol from 10deacetylbaccatin (III) through a series of chemical transformations. Since 10deacetylbaccatin III is more readily available from a natural source than taxol itself and the yew leaves from which the compound can be isolated are regenerated quickly, 10-deacetylbaccatin III can be used as a potential precursor of taxol.

Fractions containing taxanes collected from RPLC, on standing for several days, crystallize out the taxane derivatives of high purity. By contrast, fractions obtained using a silica gel column or a Florisil column pursuant to the prior art would not crystallize any taxane derivatives.

The isolation and purification method of this invention permits a highly efficient recovery of taxane derivatives in pure form from a naturally occurring Taxus species. The improvement with this invention over the prior art is reflected in the high overall recovery yield of the taxanes, e.g., 0.02–0.06% in the case of taxol, as opposed to about 0.01% in the prior art, as well as the purity of the taxanes isolated. Several other notable advantages associated with this invention are that: the reverse phase column employed has a very high capacity in terms of the ratio of silica to sample; the reverse phase column can be used repetitively, unlike a normal silica gel or Florisil column; and the reverse phase column allows the separation of taxol and its analogues with varying polarity, while polar analogues of taxol tend to be adsorbed on a silica or Florisil column. Particularly, it is possible to use an almost 3:1 to 10:1 ratio of the packing reverse phase silica to the sample amount charged on a column. This compares very favorably with the 85:1 ratio obtained when using a Florisil column. Additionally, the second aspect is reflected in an economic advantage of this invention over the prior art.

It is especially noteworthy that the subject process was carried out successfully on a pilot plant scale with even better results than seen in the laboratory scale. The yields of taxol ranged from 0.02–0.04%.

In a 1992 collaborative study with the National Cancer Institute which directly compared the subject process with the Polysciences procedure (which exemplifies the use of normal phase chromatography), the subject process was found to produce: (i) twice the yield of taxol; (ii) taxol of higher purity; and (iii) simultaneous isolation of two other important analogues. The process yields the following analogues: 10-deacetylbaccatin III (0.02%); 10-deacetyl taxol-7-xyloside (0.06–0.1% ); taxol-7-xyloside (0.005%); 10-deacetyl taxol (0.008%); and three other taxanes. Up to now, the only precursor for the semi-synthesis of taxol has been the 10-deacetyl baccatin III. The last three compounds named above are now added to the list as new precursors. When one adds the yield of directly isolated taxol to the taxol made from these four precursors, the total yield of taxol approaches 0.1%, an 8-fold to 10-fold increase.

Recently, isolation of the xyloside analogues has been reported by other researchers (International Congress on Natural Products Research, Nova Scotia, Jul. 1994). However, the procedures used in these reports are considerably more involved, as compared to the single column method we use for their isolation.

Figure 4A:
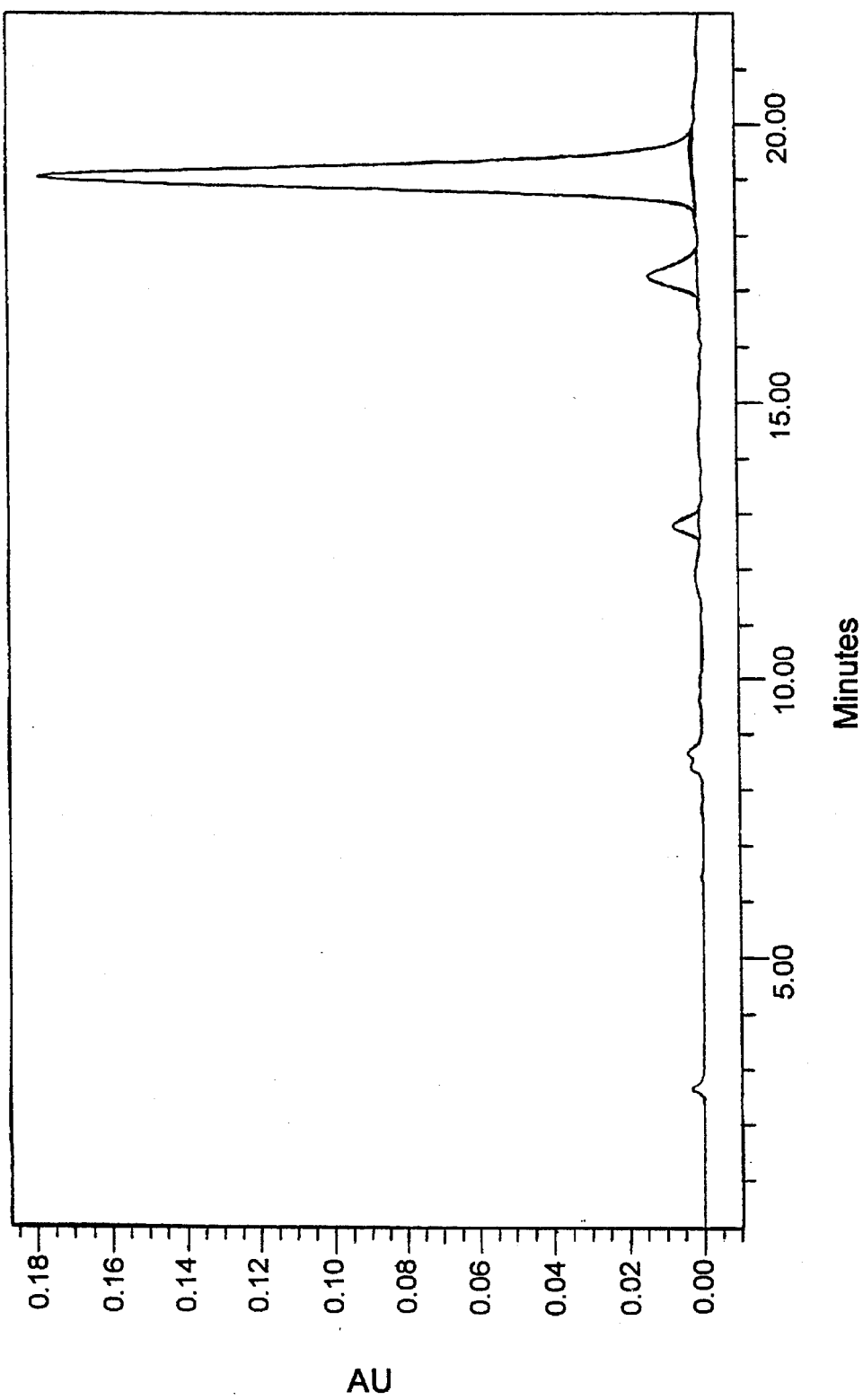
FIGS. 4a and 4b show the HPLC patterns of the taxol/cephalomannine mixtures before the ozone treatment and after the ozone and crystallization, respectively.
Figure 4B:
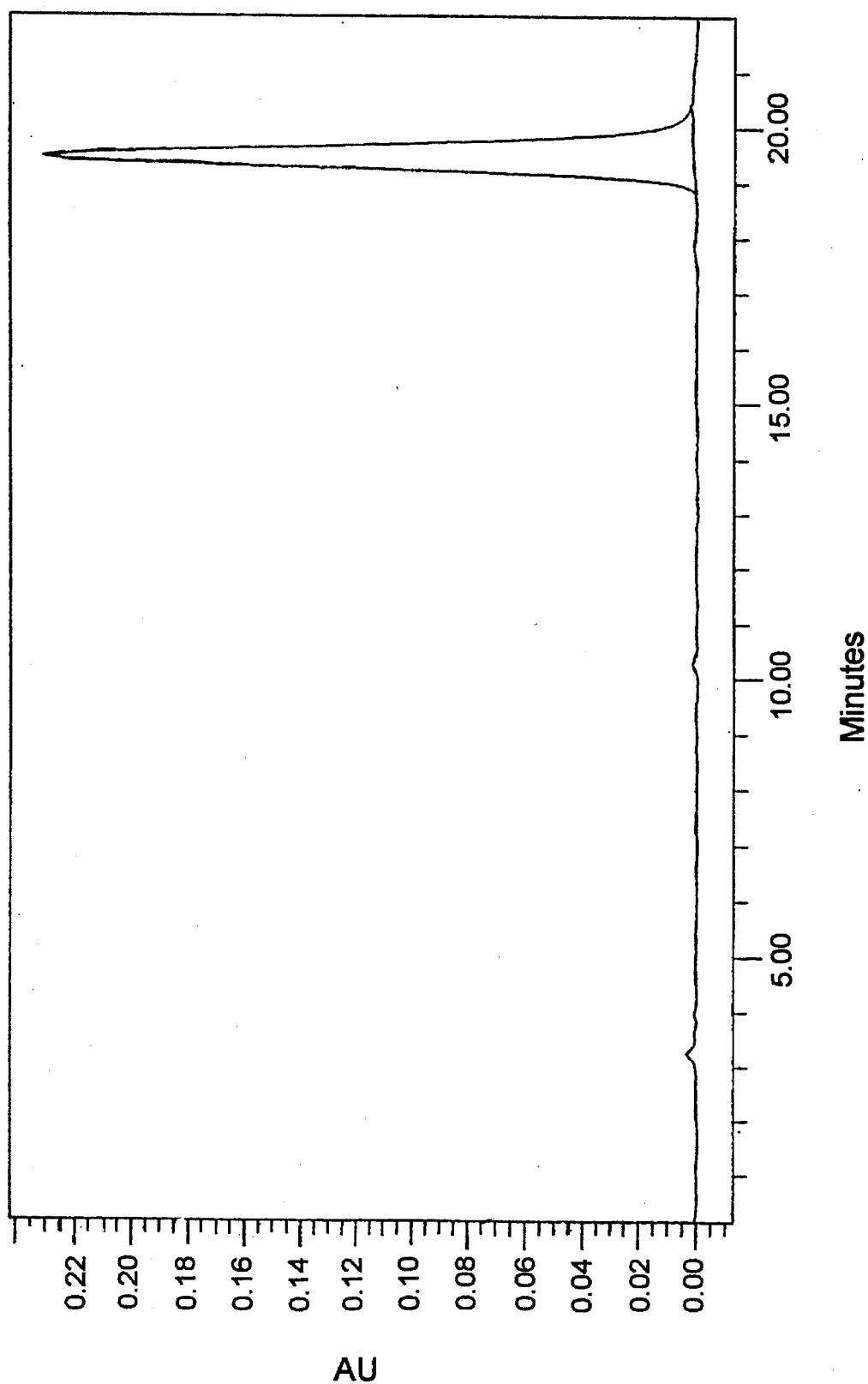

One of the main problems in the isolation of taxol from the bark of *T. brevifolia* is the accompaniment of taxol by cephalomannine. It is the removal of cephalomannine from the taxol that takes much of the effort in the currently used processes. We have developed a method for this separation by using ozonolysis. Taxol is found to be inert to ozone, while cephalomannine reacts with ozone to form a different product, which can be more readily separated from taxol. This method has been tried a number of times and found to work efficiently. FIGS. 4a and 4b show the HPLC patterns of the taxol/cephalomannine mixtures before the ozone treatment and after the ozone and crystallization, respectively.

A chemical method for the separation of taxol and cephalomannine was published by Kingston et al. (1992) using osmium tetroxide, which, again, reacts with cephalomannine to produce a more polar compound, while taxol does not react.

The use of ozone has the following advantages over this method: (1) Ozone is almost inexpensive compared to osmium tetroxide. (2) Ozone is also relatively nontoxic compared to osmium tetroxide. While ozone may not leave any traces in the final product, it is important to make sure that the osmium is completely removed from the clinical samples of taxol. (3) When used with the crude mixtures of the taxol/cephalomannine (and others), ozone causes bleaching of the colored impurities, thus facilitating the purification of taxol. This is an especially important feature when crude taxol obtained from the subject reverse phase column procedure is used as the starting material.

The procedure using ozone to cleave a non-tetrasubstituted double bond is well known. In the subject process the analogues which have non-tetrasubstituted double bonds, e.g., in the side chain of cephalomannine, the 4/20 double bond of brevitaxane and taxanes I–IV, or the cinnamoyl moiety of taxane I–IV, are susceptible to reaction with ozone, i.e., are ozone-reactive.

The subject reverse-phase column process will work best for the separation and purification of not only taxol but also some of its analogues, e.g., xylosides that may be present. The taxane xylosides do not elute easily from normal-phase silica gel columns and are effectively lost in such processes unless more highly polar solvents are used. However, under these conditions, many "colored" impurities also elute. These colored impurities are not removed by, and do not interfere with, the subject reverse-phase procedure. These impurities can be removed at a later stage, if desired. The fact that such xylosides can be eluted from the subject single-column process is advantageous. In addition, these xylosides can be used in known chemical conversion methods to obtain additional amounts of taxol, thus increasing the yield even more.

Additionally, separation of cephalomannine and taxol, which takes much effort in the existing processes, can be simplified by the use of ozonolysis. Thus, a combination of the reverse-phase column and use of ozone for the removal of interfering taxaries will be of value not only for the current process starting with the bark, but also for the future processes that start with the needles of *T. baccata* or *T. x media Hicksii*, or for the tissue culture method of production. Simplicity, improved yields, simultaneous availability of several analogues which can be recycled into taxol, and even economical operation are all factors which show the advantages and superiority of the subject process.

Accordingly, this invention provides an attractive solution to the serious supply problem of taxol by furnishing high quantities of taxol and natural analogues which can be chemically transformed to taxol.

Following are examples which illustrate procedures, including the best mode, for practicing the invention. These examples should not be construed as limiting. All percentages are by weight and all solvent mixture proportions are by volume unless otherwise noted.

EXAMPLE 1

Step 1. Extraction. The plant material: the bark, needles, wood, roots, or a combination, may be used either fresh or dried. Drying implies only air-drying at ambient temperature. The plant was extracted with methanol or ethanol at room temperature by soaking for 6–24 hours, with a volume of solvent enough to cover the plant material. The extraction may be speeded up by having the extract returned to the tank continuously in the form of a spray. By this method, the extract reaches a constant value in 4–6 hours, when monitored by UV absorbances at 275 nm. After leaving for an additional 12–15 hours (without recycling), the extract was drained and the process repeated three or four times. The combined extract was concentrated under reduced pressure (<35°–40° C.) to remove most of the alcohol.

Step 2. Partition. The concentrate was partitioned with chloroform (or dichloromethane, dichloroethane, trichloroethane) to selectively extract taxol and its natural analogues into the organic solvent, leaving the bulk of the hydrophilic constituents in the aqueous layer. In general, from the methanolic extract of the bark or the wood, only about 5–10% of the total UV-absorbing constituents passed into the solvent layer. From the extract of the needles, 20–40% of the UV-absorbing constituents pass into the organic layer. No defatting of the concentrate by selective partitioning with solvents was necessary.

The combined chloroform extract was concentrated under reduced pressure to a thick syrup and the syrup poured into glass dishes and dried in a vacuum oven (<40° C.) to a powder (if bark or wood was used), or to a glass (when needles were used). From 100 kg of the bark or wood, the yield of the extract was 1.5–2.5 kg and from needles, 2.4–4.8 kg. This sample is called the chloroform extract solids. No selective extraction was necessary for the removal of the fats and waxes.

Step 3. Chromatography. Into a stainless steel column (6" diam.×6' long) was poured a slurry of 12–14 kg of C-18 bonded silica (15–35 micron) in methanol. After the column has settled while the solvent was being pumped at 20–80 p.s.i., the methanol was replaced with 25% acetonitrile in water until the column was equilibrated.

A sample of the chloroform extract solids (2–2.5 kg) was dissolved in acetonitrile (5 L), warming it if necessary. While the thick solution was being stirred, water (5 L) was added, followed by the equilibrated silica gel (approx. 2–3 L of the slurry). As the stirring continued, more water (approx. 15 L) was added gradually. The mixture was stirred for another 15 minutes and let stand for 15–30 minutes. The clear supernatant was siphoned off and the thick slurry of the silica gel which now was impregnated with the sample, was transferred onto the top of the column. The container was rinsed with part of the supernatant and the slurry transferred to the column. The rest of the supernatant was added to the column as much as there was room. The column was then sealed and the remaining supernatant pumped into it, as the column was started to flow. After the sample addition was completed, the column was eluted with a step gradient of 35, 40, 45, 50, and 55% acetonitrile/water, using about 40–50 liters for each solvent mixture. Fractions of approx. 2 L were collected with the pressure maintained between 20–80 p.s.i. After the 55% acetonitrile, the column was washed with methanol (50 L), followed by a mixture of methanol/ethyl acetate/ligroin (2:1:1) until the effluent, which was initially very dark, became colorless. After this the column was washed again with methanol, followed by 25% acetonitrile in water, at which point it was regenerated and ready for a new run.

Processing of the taxol analogue components of the bark of *T. brevifolia*. The fractions were all monitored by UV absorbance at 275 ran, analytical HPLC and TLC. Based on these results, the fractions containing taxol and the various important taxol analogues were located and these fractions were set aside in a hood, where slow evaporation of the solvent took place. Crystals began forming in 1–2 days and the process was allowed to continue for 8–10 days. Crystallization was observed in six different regions of the fractions collected.

The crystals from these six regions were filtered in groups based on the HPLC patterns, and the resulting solids airdried. Based on the major component (HPLC/TLC patterns), the crystals could be grouped into the following regions:(1) 10-deacetyl baccatin III; (2) 10-deacetyl cephalomannine-7-xyloside; (3) 10-deacetyl taxol-7-xyloside; (4) 10-deacetyl taxol-C-7-xyloside/taxol-7-xyloside and 10-aleacetyl taxol; (5) cephalomannine/taxol and beta sitosterol/beta sitosterol-D-glucoside. Other fractions contained a variety of taxol analogues but most of them did not crystallize out directly. Each of the crystalline solids was processed as described below. The amounts are based on the use of 100 kg of bark.

Step 4. Purification.

10-Deacetyl baccatin. The crude crystals from this region (26 g) were recrystallized from acetone using charcoal to give 18 g of pure compound, identical with an authentic sample of 10-deacetyl baccatin III. Additional amounts (3 g) could be obtained from the filtrate after a short silica column in chloroform and elution with 2–5% methanol in chloroform. Yield 0.02%.

10-Deacetyl cephalomannine-7-xyloside. The crude crystals from this region (30 g) after recrystallization from acetone yielded 6 g of the pure 10-deacetyl cephalomannine-7-xyloside (0.006%). The identity was confirmed by analytical and spectral data.

10-Deacetyl taxol-7-xyloside. The crude crystals (180 g) from this region were recrystallized from acetone to provide 99 g of the pure xyloside, identical with an authentic sample, yield, 0.1%.

10-Deacetyl taxol-C-7-xyloside. The crude crystals of this region (98 g) when recrystallized twice from acetone gave the pure 10-deacetyl taxol-C-7-xyloside (40 g, 0.04%). Its identity was confirmed by analytical and spectral data.

10-Deacetyl taxol. The filtrate from the crystallization of 10-deacetyl taxol-C-7-xyloside contained 10-deacetyl taxol and taxol-7-xyloside as the major components. This mixture was chromatographed on a silica gel using chloroform and eluted with 2% methanol and 5% methanol in chloroform respectively. The former yielded on concentration and crystallization from acetonitrile, 10-deacetyl taxol, 8 g (0.008%). It was identical with an authentic sample.

Taxol-7-xyloside. Fractions from the above column obtained by elution with 5% methanol, after concentration and crystallization from acetone, gave pure taxol-7-xyloside, 8 g (0.008%), the identity of which was confirmed by analytical and spectral data.

Cephalomannine. The crystals from the region cephalomannine/taxol were divided into two parts. The earlier part (25 g) contained 10% or higher of cephalomannine, the rest being taxol. The later fractions (110 g) contained less than 5% of cephalomannine. The two were processed separately.

The earlier fraction (25 g) was purified by a repeat of the reverse phase column chromatography on C-8 bonded silica (625 g) using 40–45% acetonitrile in water. The sample was dissolved in acetonitrile (50 ml), stirred with equilibrated C-8 silica (100 ml), and diluted with water (150 ml) and the slurry added to the column. Elution was first with 40% acetonitrile/water and later, 45% acetonitrile/water. Fractions of 100 ml were collected, tested by analytical HPLC, and let stand for a week. The crystals that separated out from the fractions containing mostly cephalomannine were filtered and recrystallized from acetone/ligroin to yield pure cephalomannine, 4 g (0.004%), identical with an authentic sample.

The second part (110 g) of the crystals which had less than 5% of cephalomannine were crystallized twice from acetone/ligroin using charcoal to yield pure taxol, 41 g (0.04%). Alternatively, the crude crystals were decolorized by passing a solution in chloroform (500 ml) through a short column of silica or Florisil (250 g). Another alternative for removing the cephalomannine contaminant is the use of ozone. Washing the: column with 1–2% methanol in chloroform gave the bulk of the taxol which was recovered by concentration and crystallization. The yield was nearly the same as before, 40 g. The HPLC analysis showed that it contained less than 0.3% of cephalomannine.

Brevitaxane (Brevifoliol). The fractions that contained 10-deacetyl cephalomannine-7-xyloside also contained other taxanes, notably, brevitaxane (also called brevifoliol), which remained mostly in solution. The xyloside was concentrated, combined with the solid from other fractions containing the same component and the solid (25 g) applied to a column of silica gel (250 g) in chloroform. Elution with 1–2% methanol in chloroform gave this compound as pure component. It was crystallized from acetone/ligroin to yield pure brevifoliol, 10 g (0.01%). Its identity was confirmed by analytical and spectral data.

EXAMPLE 2

Dried needles of *Taxus x media* Hicksii (200 lbs.) were extracted with methanol three times as described and the extract concentrated to remove most of the methanol to a volume of approximately 25 gallons. The aqueous concentrate was extracted with chloroform three times using 20, 15, and 10 gallons of chloroform and the combined chloroform extract concentrated under reduced pressure. The concentrate was poured into a glass tray and kept in a vacuum oven (<40° C.) until the last traces of chloroform were removed, resulting in a dark green glassy solid, 4.8 kg.

The extract solids (2–2.5 kg) were dissolved in acetonitrile (5 L) and while being stirred, were diluted with water (5 L). To this mixture was added C-18 silica gel (3 L) pre-equilibrated with 35% acetonitrile in water. While the stirring was proceeding, water (15 L) was added and the mixture stirred for another 15–20 minutes and the clear supernatant decanted off into another container. The slurry of the silica containing the sample was added to the column, using the supernatant to rinse the container and transfer the suspension. The supernatant was added until the column as full, the top was clamped, and the rest of the supernatant pumped into the column while the column started to run. This was followed by introducing a step gradient of 35, 40, 45, 50, and 55% acetonitrile/water, with 50 L of each solvent mixture.

Fractions of 2 L were collected and these were monitored by UV absorbance at 275 nm, TLC, and analytical HPLC. Those fractions which showed strong presence of some of the taxaries were separated from the others and kept in a hood, where slow evaporation took place and crystalline taxanes started to separate out. After 8–10 days, the crystalline solids were filtered in groups based on the HPLC data and the solids air-dried.

The column was washed with methanol (50 L), followed by a mixture of methanol/ethyl acetate/ligroin (2:1:1) until the effluent, which was initially dark, became colorless. After this, the column was washed with methanol and equilibrated with 25 % acetonitrile in water, at which time it was ready for the next run. The crude crystalline solid from the taxol region contained other taxanes which co-eluted, although most of these could be separated by careful monitoring of the fractions by HPLC and filtering the solids separately from each individual fraction.

In earlier experiments, these taxol analogues were purified by crystallization and characterized. The major components were found to be the ones represented by the structures shown below:

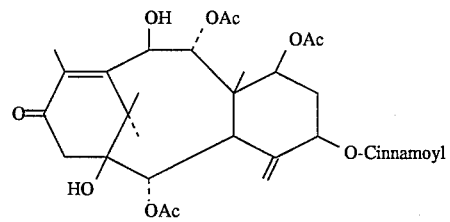

Taxane I from Taxus x media Hicksii

-continued

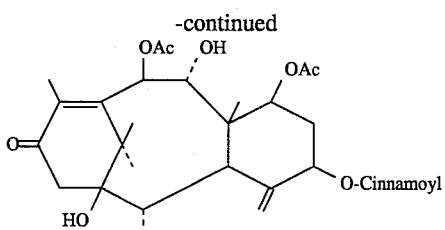

Taxane II from Taxus x media Hicksii

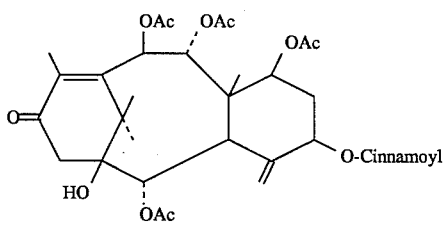

Taxane III from taxus x media Hicksii

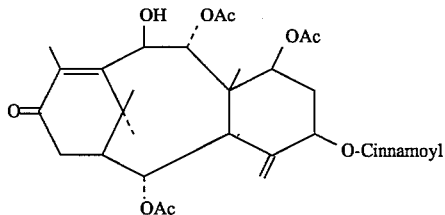

Taxane IV from taxus x media Hicksii

When Taxane I was subjected to the described ozonolysis procedure, the resulting compound was that having the structure shown below:

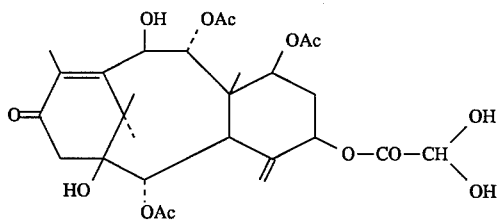

Product of ozonolysis from taxane I from *Taxus x media* Hicksii In the other taxanes (II, III, and IV), the same changes take place: conversion of

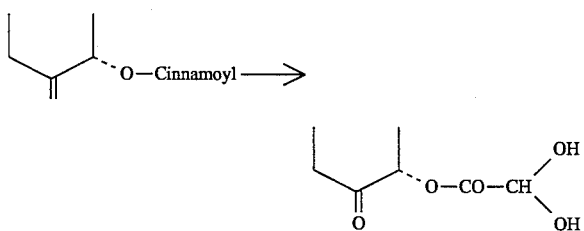

Of these, taxanes I and II were the ones which co-eluted with taxol. For final purification, the solids that contained mixtures of these taxanes I and II (with minor amounts of taxane III and brevifoliol) and taxol were subjected to ozonolysis in chloroform/methanol (4:1) at –70° C. (dry ice and acetone). For example, 25 g of the mixture in 250 ml of the solvent mixture was cooled to –70° C. and ozone from an ozone generator (Ozone Equipment and Research Corporation, Phoenix, Ariz.) was bubbled through the solution at a gauge pressure setting of 3–6. The original dark solution soon turned much paler, with the blue color due to the ozone giving a pale brownish blue color. Monitoring by HPLC showed that the taxanes I, II, III, and brevifoliol were absent, being replaced by other peaks, but the peak due to taxol was unchanged. Monitoring by TLC was also carried out, with the plates being sprayed with a solution of starch/potassium iodide. The ozonides gave a blue spot by the oxidation of the iodide to iodine, which gave a blue color with starch. The ozonation took 20–40 minutes at –70° C. and the HPLC analysis, about 20 minutes. At this point, the ozone and the ozonides formed were decomposed by the addition of dimethyl sulfide (10 ml) and the mixture let stand for 2–12 hours. The decomposition of the ozonides was verified by TLC, in which the starch/iodine was negative.

The ozone reacted selectively with these taxanes which contain olefinic double bond(s). Brevifoliol is cleaved at the 4/20 double bond to form the ketone shown in the structure. Taxanes I, II, and II contain not only the 4/20 double bond but also an additional double bond in the cinnamate ester side chain. The latter is cleaved to an aldehyde which readily forms a hydrate shown in the structure. Although these compounds as well as taxol contain a double bond at 11/12 position, this is a tetrasubstituted double bond and is generally inert to ozone under these conditions. Besides dimethyl sulfide, other well-known reagents may be used for the reductive decomposition of the ozonides, as for example, trimethyl phosphite, zinc dust, sodium (or potassium) iodide, ascorbic acid, etc. However, dimethyl sulfide, in spite of its malodorous property, is a volatile chemical and is readily eliminated during the concentration. Reaction of dimethyl sulfide with ozone leads to dimethyl sulfoxide which can be readily removed by partition between water and chloroform, the taxanes being soluble in the chloroform.

After the removal of the dimethyl sulfoxide by partition, the solvent layer was concentrated and the solid (25 g) in chloroform (200 ml)applied to a column of silica (230–425 mesh, 250 g) in chloroform. Elution with 2–5% acetone gives the bulk of the taxol, which is recovered and purified by crystallization from acetone/ligroin or acetonitrile/water. The taxol so obtained is completely free from the accompanying taxane impurities as shown by the HPLC trace and spectral data.

Although these taxanes can be separated from taxol without the ozonation, by silica column chromatography, it will require at least two such columns for the complete removal of these compounds. The ozone reaction permits a more complete purification in one column.

EXAMPLE 3

The dried ground bark (1 kg) of *Taxus brevifolia* was extracted three to five times by percolation with 95% ethanol. The ethanol extract was concentrated at reduced pressure (15–25 mm at 35°–48° C.) to a brown syrup concentrate and partitioned between 1 L of water and 1 L of chloroform. After equilibration, the chloroform phase was separated and the aqueous phase was extracted twice with chloroform. The combined chloroform extract was dried over sodium sulfate and concentrated at reduced pressure to dryness. A solid material (15 g) was obtained.

The extracted solids were chromatographed on a preparative scale (30 ×300 mm) reversed phase $C_{18}$ column. The column was packed with about 100 g of $C_{18}$-silica. The eluant was a gradient of acetonitrile in water (e.g., 20, 25, 30, 35, 40, 45, 55, and 80% acetonitrile) at a flow rate of 6–12 ml/minute. Elution of peaks was monitored at 275 nm or by thin layer chromatography (silica plates, 5–10% methanol in chloroform; visualization by UV light as well as spray with 0.1–1.0 N $H_2SO_4$ followed by gentle heating on a hot plate) and by analytical HPLC ($C_{18}$-silica, 40–50% acetonitrile in water as the eluant at 1 ml/minute).

A 10 g sample of the solid was dissolved in 10–15 ml of acetonitrile and the solution diluted with 50 ml water at 45°–55° C. to give a 20–30% acetonitrile suspension. The resulting milky solution was applied to the column. The column was first eluted with 20% acetonitrile in water in 50–70 fractions of 15–20 ml each. After these fractions were collected, the column was eluted with an increasing concentration of acetonitrile in water in 100 fractions of 15–20 ml each. Finally, the column was eluted with 80% acetonitrile in water and washed with a mixture of methanol, ethyl acetate, and ligroin (50:25:25). The column was reequilibrated with acetonitrile/water (1:4) for reuse). Fractions 1–15 were combined and concentrated to dryness to yield a mixture of taxanes. Fractions 16–28 on concentration and trituration of the solid with 30–50% acetonitrile-water gave a crystalline solid which was filtered and recrystallized from acetone-hexane (1:1) to give a colorless crystalline solid identified as 10-deacetylbaccatin III, yield 0.3 g, m.p. 232°–234° C.

IR (KBr): 3470, 3430, 1716 $cm^{31}$. NMR ($CDCl_3$/DMSO): 1.00 (S, 6H, 1.63 (S, 3H), 1.95 (S, 3H), 2.24 (S, 3H), 3.83 (d,J=7 Hz,1H), 4.47 (d, J=3 Hz, 1H), 5.18 (d, J=3 Hz, 1H), 5.44 (d,J=7Hz, 1H), 7.5(d, J=7 Hz, 3H), 8.01 (d, J=7 Hz, 2H).

Elemental analysis calculated for $C_{29}H_{36}O_{10}$:C, 63.96; H, 6.66%. Found: C, 63.82; H,6.59%.

Fractions 40–50 on concentration gave a taxane identified as 10-deacetylcephalomannine-7-xyloside, yield 0.1 g, m.p. 202–252 (dec.).

IR (KBr): 3420, 2930, 1740–1710, 1660, 1600, 1585 $cm^{-1}$. NMR($CDCl_3$): 0.857 (s, 3H), 1.177 (s, 3H), 1.262 (br, s, 6H), 1.577 (m, 1H), 1.740 (s, 3H), 1.899 (s, 3H), 2.174–2.255 (m, 2H), 2,363 (m, 3H), 2.580–2.676 (m,1H), 3.015(t,1H),3.162(d,1H),3.320(t,1H,3.795–3.855(m,1H), 4.057–4.293(m,2H), 2.545, 4.557 (d, 1H), 4.906, 4.936 (d, 1H), 5.330 (s, 1H), 5.461–5.502 (dd, 1H), 6.126(t, 1H), 7.271–7.379 (m, 1H), 7.364, 7.379 (d, 4H), 7.499–7.689(m, 5H), 7.864, 7.894 (d, 1H), 8.069 (d, 2H).

Elemental analysis calculated for $C_{48}H_{59}NO_{17}.H_2O$: C, 61.54; H, 6.50; N, 1.48%. Found: C, 61.62; H, 7.05; N, 1.42%. Fractions 60–75 on concentration gave a taxane identified as 10-deacetyltaxol-7-xyloside, yield 1 g, m.p. 245°–248° C., optical rotation −1° '(in pyridine).

IR (KBr): 3540, 3420, 1750, 1720, 1710, 1645, 1600, 1580 $cm^-$. NMR (DMSO): 1.123 (s, 3H), 1.180 (s, 3H), 1.205–1.259 (m, 2H), 1.582 (m, 1H), 1.691 (m, 1H), 1.780 (s, 6H), 1.895 (s, 3H), 1.944–2.028 (m, 2H), 3.0–3.212(m, DMSO),3.513(m,1H),3.594(br,s,1H),3.836–3.850(d,2H), 3.870,3.891(d,1H), 4.075, 4.098 (m, 1H), 4.135, 4.201 (m, 1H), 4.21–4.283 (m, 2H), 4.511–4.603 (br, m, 1H), 4.620, 4.713 (d, 1H), 4.294, 4.956 (d, 1H), 5.305 (s, 1H), 5.518–5.543 (m, 1H), 5.624, 5.849 (d, 2H), 5.743, 5.765 (br, d, 1H), 6.166, 6.194, 6.223 (t, 1H), 7.268, 7.281, 7.316 (m, 1H), 7.364–7.409 (m, 4H), 7.493–7.542 (m, 5H), 7.587, 7.811, 7.635 (m, 2H), 7.844, 7.869 (d, 2H), 8.102–8.193 (m, 2H), 8.163, 8.183 (d, 1H).

$^{13}C$ NMR: 10.406, 13.456, 20.655, 22.314, 26.620, 34.805, 34.955, 38.677, 38.958, 39.235, 39.511, 39.760, 40.068, 40.343, 42.843, 46.209, 55.669, 56.221, 56.887, 57.106, 57.219, 60.747, 61.635, 61.733, 62.130, 63.201, 65.658, 66.429, 69.093, 69.819, 73.115, 73.545, 74.150, 74.479, 75.265, 76.476, 76.853, 80.072, 80.659, 83.271, 102.898, 102.948, 102.997, 103.173, 103.249, 104.627, 127.019, 127.280, 128.124, 128.527, 129.434, 129.942, 131.169, 133.229, 134.419, 136,053, 136.383, 139.241, 165.137, 166.169, 169.774, 172.548, 208.196.

Elemental analysis calculated for $C_{50}H_{57}NO_{17}.H_2O$: C,62.88; C, 62.88; H, 6.10; N, 1.43%. Found: C, 62.94; H, 6.02; N, 1.58%.

The m.p. optical rotation and $^1H$ NMR spectra agreed with those reported by V. Senilh et al. (1984)*J. Nat. Prod.* 47:131.

Fractions 85–90 on concentration gave a taxane identified as brevitaxane A, yield 0.1 g, m.p. 220°–222° C., optical rotation −27° (in chloroform).

IR (KBr): 3570, 3400, 2980, 2930, 1740–1730, 1655, 1590 $cm^-$. NMR ($CDCl_3$): 0.899 (s, 3H), 1.039 (s, 3H), 1.267 (m, 1H), 1.343 (s, 3H), 1.50 (d, 1H), 1.743 (s, 3H), 1.87 (m, 1H), 2.008 (s, 3H), 2.075 (s, 3H), 2.318 (m, 1H, 2.466 (m, 1H), 2.677 (s, 1H), 2.746 (d, 1H), 4.380 (br, s, 1H), 4.440 (s, 1H), 4.690 br, s 1H), 4.823 (s, 1H), 5.180 (s, 1H), 5.565 (dd, 1H), 6.06 (d, 1H), 6.522 (d, 1H), 7.429 (m, 2H), 7.554 (m, 1H), 7.861 (d, 2H).

$^{13}C$ NMR (DMSO): 11.727, 11.957, 20.559, 21.258, 26.405, 27.088, 28.008, 36.511, 38.848, 44.652, 46.657, 61.168, 69.283, 69.594, 70.639, 74.663, 75.165, 77.291, 109.690, 128.677, 129.222, 129.771, 133.221, 134.001, 150.311, 151.271, 164.138, 169.162, 169.337.

Elemental analysis calculated for $C_{31}H_{40}O_9$:C,66.89;H, 7.24%. Found: C, 67.13; H, 7.35%.

Fractions 100–115 on concentration gave a taxane identified as 10-deacetyltaxol, yield 1.0 g, m.p. 192°–196° C.

IR (KBr): 3430, 2920, 2840, 1740–1710, 1650, 1600, 1575, 1520 $cm^-$. NMR ($CDCl_3$): 1.10 (s, 3H), 1.19 (s, 3H), 1.42 (s, 3H), 1.74 (s, 3H), 1.872 (m, 1H), 2.275 (m, 1H), 2.375 (s, 3H), 2.5 (m, 1H), 3.74, 3.76 (d, 1H), 3.868, 3.891 (d, 1H), 4.18–4.315 (m, 2H), 4.77 (dd, 1H), 4.93 (d, 1H), 5.18 (s, 1H), 5.67 (d, 1H), 5.76 (dd, 1H), 6.176 (t, 1H), 7.16 (d, 1H), 7.388–7.529 (m, 9H), 7.76, 7.784 (d, 2H), 8.099, 8.125 (d,2H).

$^{13}C$ NMR ($CDCl_3$)L 9.907, 14.307, 20.656, 22.581, 26.614, 26.969, 36,061, 37.070, 43.114, 46.556, 55.116, 57.791, 72.026, 72.486, 73.336, 74.580, 74.951, 78.854, 81.231, 84.178, 127.079, 128.310, 128.693, 128.716, 129.975, 129.324, 130.195, 130.259, 131.898, 133.663, 133.817, 138.054, 138.112, 166.978, 167.019, 170.439, 172.544, 211.270.

Fractions 120–130 on concentration gave a taxane identified as taxol-7-xyloside, yield 0.1 g, m.p. 236°–238° C.

IR (KBr): 3400, 1740, 1650, 1590, 1520 $cm^-$. NMR ($CDCl_3$): 1.2 (s, 6H), 1.76 (s, 3H), 1.85 (s, 3H), 2.15 (m, 1H), 2.22 (s, 3H), 2.75 (m, 2H), 3.27 (br, s, 2H), 3.63 (m, 2H), 3.84 (m, 2H), 4.21 (br, s, 2H), 4.32 (m, 2H), 4.79 (s, 1H), 4.90 (d, 1H), 5.68 (d, 1H), 5.79 (d, 1H), 6.10 (t, 1H), 6.38 (s, 1H), 7.03 (d, 1H), 7.40–7.60 (m, 11H), 7.74 (d, 2H), 8.12 (d, 2H).

$^{13}$CNMR ($CDCl_3$): 11.02, 14.60, 21.04, 22.65, 26.50, 35.24, 35.70, 43.20, 46.76, 55.09, 57.881, 64.40, 69.32, 72.11, 72.19, 73.25, 74.63, 76.08, 76.77, 77.10, 77.61, 78.62, 79.34, 81.29, 83.86, 127.07, 128.34, 128.70, 129.00, 130.19, 131.93, 133.80, 133.72, 138.07, 140.03, 166.92, 167.09, 170.59, 172.61, 201.98.

Fractions 160–165 on concentration gave a solid which was recrystallized twice from acetonitrile:water (1:1) to give cephalomannine, yield 0.04 g, m.p. 184°–186° C.

Identification of cephalomannine was carried out by comparison between chromatographic characteristics (TLC, HPLC) of the sample thus obtained and those of an authentic sample, as well as by other spectroscopic comparison, i.e., IR, NMR, OR, etc.

Fractions 175–195 when similarly concentrated and the solid recrystallized twice from acetonitrile:water (1:1) gave taxol as a colorless, crystalline solid, yield 0.4 g, m.p. 212°–214° C., optical rotation −49°(1% in chloroform).

IR (KBr): 3450 (broad), 1730, 1710, 1650 cm⁻.

NMR (CDCl$_3$/DMSO): 1.18 (S, 6H), 1.64 (S, 3H), 1.89 (S, 3H), 2.17 (S, 3H), 2.38 (S, 3H), 3.80 (t, 1H), 4.66 (m, 1H), 4.90 (d, 1H), 5.65 (t, 1H), 6.19 (m,1H),6.28(S, 1H), 7.22–8.24 (m, 15H).

Elemental analysis calculated for $C_{47}H_{51}NO_{41}$:C, 66.10; H, 6.02; N, 1.64%. Found: C, 66.21; H, 6.04; N, 1.63%.

Mother liquors from the recrystallization of 10-deacetylbaccatin III were rechromatographed on RP C-8 column using 20–30% acetonitrile/water and increasing to 40–50% acetonitrile/water. Fractions containing the major peak corresponding to 10-deacetylbaccatin III were combined, concentrated, and the solid recrystallized as before to give an additional 0.1 g for a total yield of 0.4 g (0.04% yield, based on plant material).

FIG. 1 outlines the above isolation procedure and the mass balance achievable therefrom.

EXAMPLE 4

The dried needles (1 kg) of *Taxus brevifolia* were extracted three times by percolation with methanol. The methanol extract was concentrated at reduced pressure (15–25 mm at 35°–45° C.to a dark green syrup concentrate. The concentrate was partitioned between 1 L of 4:1 methanol:water and 1 L of ligroin. The aqueous methanol phase was diluted with water (1 L) and extracted first with benzene (twice) and then with chloroform. The benzene extract was dried over sodium sulfate and concentrated at reduced pressure to dryness. The solid material (8 g) was thus obtained.

The solid was chromatographed as described under Example 3 except that RPLC C$_8$ silica (100 g) was used in methanol/water 20%. A pressure of 50 p.s.i. was used to obtain an adequate rate. One hundred fifty fractions of 10 ml were collected, while a gradient of 25, 35, 45, 55, and 65% methanol in water was being used. The fractions were monitored as before, and fractions containing 10-deacetylbaccatin III (fractions 25–35), brevitaxane A (fractions 60–90), cephalomannine (fractions 120–125), and taxol (fractions 135–150) were combined separately, concentrated to dryness, and recrystallized from chloroform:hexane (1:1) to give the pure compounds 10-deacetylbaccatin III, brevitaxane A 2.0 g (0.2% yield, based on plant material), cephalomannine 0.03 g (0.003% yield, based on plant material), and taxol 0.1 g (0.01% yield, based on phmt material).

The chloroform extract solids (10 g) were likewise chromatographed on RPLC C$_8$ silica using 20% methanol/water which was raised to 65% methanol/water. Fractions containing 10-deacetylbaccatin III were concentrated and the product crystallized as before to yield an additional amount of 10-deacetylbaccatin III, providing a total combined yield of 0.2 g (0.02% yield, based on plant material).

Figure 2:
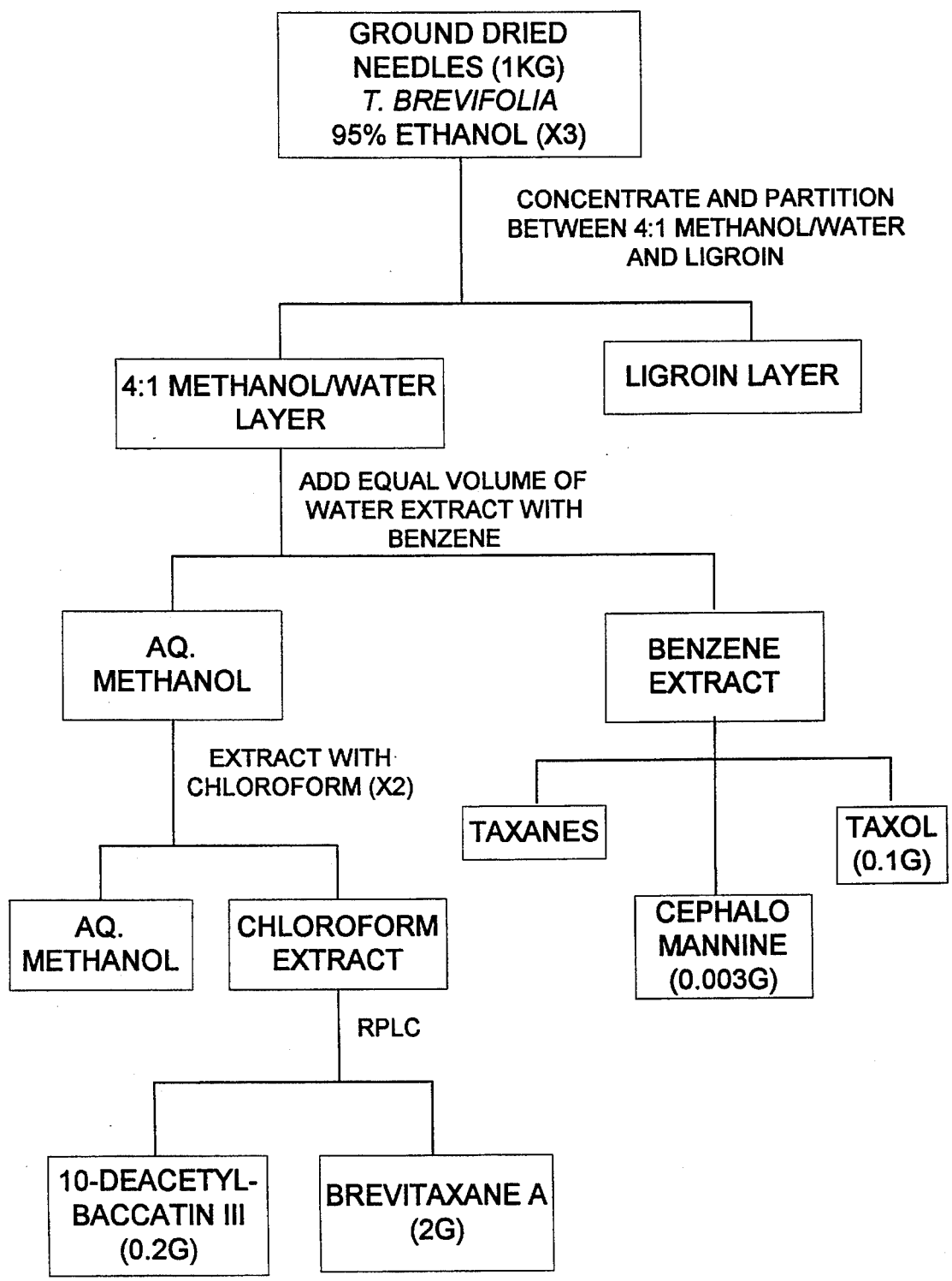
FIG. 2 shows another separation scheme for isolating taxanes from *Taxus brevifolia* in accordance with this invention.

FIG. 2 outlines the above isolation procedure and the mass balance achievable therefrom.

EXAMPLE 5

The extraction procedure of Example 4 was repeated, except that the aqueous methanol extract was further extracted with chloroform. The chloroform extract was dried over sodium surfate and concentrated at reduced pressure to dryness. The solid obtained (10 g) was chromatographed on RPLC CN-bonded silica (150 g) in acetonitrile/water 30–40% using substantially the same conditions as those described in Example 3. Fractions containing 10-deacetylbaccatin III, brevitaxane A, cephalomannine, and taxol were separately collected and the four compounds isolated. The yields were approximately the same as those given in Example 4.

EXAMPLE 6

The methanol extract (from approximately 90 lbs. of the needles of T. brevifolia) obtained according to the procedure of Example 4 was partitioned between 10 L of water and 10 L of chloroform. After two more extractions with chloroform, the combined chloroform extracts were concentrated to yield a dark green viscous mass (1200 g). Of this, 250 g was dissolved in 70–80% methanol and 5–10% acetone (total 1 L) to make a 25% solution. This solution was passed through an RP-C$_{18}$ column (approx. 500 g of the adsorbent) equilibrated in the same solvent mixture. Nearly all of the chlorophylls and waxes (which account for approx. 50% of the total weight) remained on the column while taxaries were eluted.

The eluate containing the taxanes was concentrated to near dryness and the resulting solid (110 g) was dissolved in 20–25% acetonitrile/water (500–600 ml) and applied to a RP-C$_{18}$ column (500 g). The column was eluted with increasing concentrations of acetonitrile in water (e.g., a step gradient: 25, 30, 35, 40, 45, 60% acetonitrile in water), and taxol, 10-deacetylbaccatin III, brevitaxane A, and cephalomannine were isolated with the yields of respective compounds being essentially the same as those given in Example 4.

EXAMPLE 7

Approximately 10 kg of the needles and small twigs (<0.5" diameter) of *T. floridana* were extracted as described in Example 4. The methanol extract was partitioned between water (3 L) and chloroform (3 L). After two more extractions with chloroform (2 L each), the combined chloroform extract was concentrated to a thick green syrup (220 g). The sample was dissolved in a mixture of methanol, acetone, and water (70–80, 5–10, and 20) and the solution passed through a column of RP-C$_{18}$ column made from 500 g of the adsorbent. The column was washed with the same solvent mixture until the UV absorbance indicated that washing was complete. The effluent and the wash were concentrated to near dryness and the residue (approx. 100 g) taken up in 20–30% acetonitrile/water (500–600 ml) and applied to a column of RPLC C$_8$ from approx. 500 g of the adsorbent. A step gradient was set up as before. Fractions of 200 ml were collected and monitored as before. On standing, the various fractions began to crystallize. After one week, the fractions containing the various components, 10-deacetylbaccatin III, baccatin VI, cephalomannine, taxol, and taxiflorine were filtered and the respective solids recrystallized. The mother liquors from each of these were separately chromatographed on small columns of silica gel and additional quantities of the components isolated. 10-deacetylbaccatin III, 0.05%; baccatin VI, 0.02%; taxol, 0.01%; and taxiflorine, 0.02%.

Baccatin VI had the following physical properties: m.p. 246°–251° C. (lit.244°–245° C., D. P. Della Casa de Marcano et al., 1975).

$^{13}$C NMR (DMSO): 12.404, 14.267, 20.440, 21.067, 22.434, 27.944, 34.215, 35.085, 42.743, 45.136, 46.409, 69.164, 70.035, 71.218, 72.623, 75.267, 76.581, 80.598, 82.827, 128.629, 129.671, 129.736, 133.334, 133.847, 165.153, 168.731, 169.401, 169.473, 170.147, 170.435.

Figure 3:
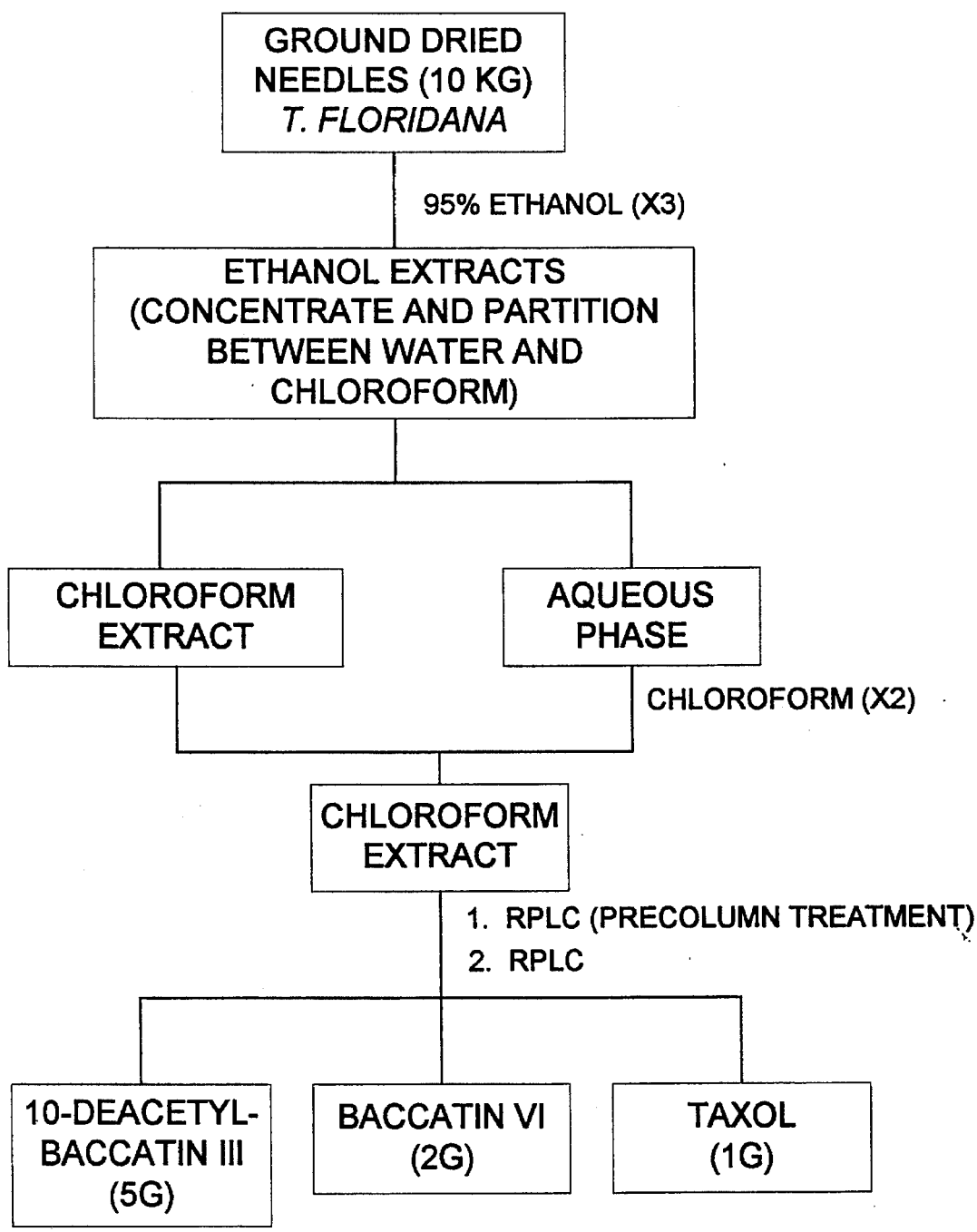
FIG. 3 shows a further separation scheme for isolating taxanes from *Taxus floridana* in accordance with this invention.

FIG. 3 outlines the above isolation procedure and the mass balance achievable therefrom.

Taxiflorine, which exists in nature and is isolated as a mixture of two isomers, is characterized as follows:

A colorless crystalline compound, m.p. 266°–268° C. Optional rotation, –26° (1% in methanol).

The NMR spectrum clearly indicates that it is a mixture of two compounds, which exist in equilibrium. As a result, "too many" peaks are seen in the spectrum. When acetylated, the acetate gives a "clean" spectrum, indicating that it is a single compound. The fact that a mixture of the two compounds giving a single acetate suggests that the original mixture was an equilibrium mixture. In this particular case (see the structure), one compound has the 7-OH and 9-OAc; the other has the 7-OAc and 9-OH. These two are situated so that the 9-OAc can swing over, transfer the acetyl to 7, and the compound becomes the other isomer. When acetylated, they both give the same compound with 7-OAc and 9-OAc. Such phenomenon have been seen frequently in taxane compounds. In fact, taxaries I and II from *Taxus x media* Hicksii comprise such a mixture. The NMR spectral data for the acetate are provided below:

Proton NMR spectrum of the acetate. 1.19, 1.63, 1.78, 1.81, 1.83, 2.01, 2.02, 2.13, 2.30, 2.68, 2.99, 4.21, 4.30, 4.97, 5.52, 5.62, 6.19, 6.32, 6.44, 7.43, 7.58, 7.93.

Carbon NMR spectrum of the acetate. 11.17, 13.2, 20.5, 20.9, 21.5, 21.6, 21.8, 24.9, 27.5, 34.6, 36.7, 43.6, 43.9, 67.50, 67.54, 67.83, 67.96, 68.05, 70.39, 74.53, 75.41, 78.62, 78.85, 84.85, 128.4, 129.42, 129.7, 133.2, 135.9, 146.9, 166.30, 167.98, 169.01, 169.99, 170.21, 170.59.

It should be understood that the examples and embodiments described herein are for illustrative purposes only and that various modifications or changes in light thereof will be suggested to persons skilled in the art and are to be included within the spirit and purview of this application and the scope of the appended claims.

References Cited

U.S. Patent Documents
U.S. Pat. No. 5,279,949.
U.S. Pat. No. 4,814,470.
Other References
Castor and Taylor (1993)*J. Liq. Chromatography* 16:723–731.
Chmumy et al. (1993) *Phytochem.* 34:477–483).
Wani et al. (1971) *J. Am. Chem. Soc.* 93:2325.
Huang, C.H.O., et al. (1986)*J. Nat. Prod.* 49:665.
Miller, R. W., et al. (1981)*J. Org. Chem.* 46:1469.
McLaughlin, J. L., et al. (1981)*J. Nat. Prod.* 44:312.
Kingston, D.G.I., et al. (1982)*J. Nat. Prod.* 45(4):466–470.
Kingston, D.G.I., A.A.L. Gunatilaka, C. A. Ivey (1992) *J. Nat. Prod.* 55:259.
Senilh, V., et al. (1984)*J. Nat. Prod* 47:131.
Denis et aL (1988) *J. Am. Chem. Soc.* 110:5817.
D. P. Della Casa de Marcano et al. (1975) *J. Chem. Comm.* 365.
Witherup et al. (1990) *J. Liq. Chrom.* 53:1249–1255.

I claim:

1. A method for isolating taxol and natural analogues of taxol, said method comprising the steps of:
   (a) treating an extract comprising taxol and the natural analogues of taxol by reverse phase liquid chromatography on a single preparative column having an adsorbent, causing said taxol and said analogues of taxol to be adsorbed on the adsorbent;
   (b) eluting, with an elutant, taxol and the natural analogues of taxol from the adsorbent; and
   (c) recovering taxol and the natural analogues of taxol in separate fractions of eluate;
   (d) treating with ozone an eluted fraction comprising an ozone-reactive taxol analogue obtained in step (c), wherein said ozone-reactive taxol analogue undergoes ozonolysis which permits improved separation of the taxol analogue from taxol; new line, insert "(e) treating the second recovered taxol and the natural analogues of taxol by a second chromatography step."

2. The method, according to claim 1, wherein the natural analogues of taxol are selected from the group consisting of taxol C, 10-deacetyltaxol C, 10-deacetyltaxol C-7-xyloside, taxol-7-xyloside, 10-deacetyltaxol, 10-deacetyltaxol-7-xyloside, cephalomannine, cephalomannine-7-xyloside, 10-deacetylcephalomannine-7-xyloside, baccatin III, 10-deacetylbaccatin III, baccatin VI, brevitaxane A, and taxiflorine.

3. The method, according to claim 1, wherein the extract is a crude extract obtained from a Taxus species.

4. The method, according to claim 3, wherein the crude extract is obtained from the needles of the Taxus species.

5. The method, according to claim 3, wherein the crude extract is obtained from the bark of the Taxus species.

6. The method, according to claim 3, wherein the Taxus species is *Taxus brevifolia*.

7. The method, according to claim 3, wherein the Taxus species is *Taxus floridana*.

8. The method, according to claim 3, wherein the Taxus species is *Taxus x media* Hicksii.

9. The method, according to claim 1, wherein the extract is obtained from in vitro culture.

10. The method, according to claim 1, wherein the extract is obtained from chemical synthesis or semi-synthesis of taxol.

11. The method, according to claim 1, wherein the extract is obtained by extraction with at least one water-miscible organic solvent.

12. The method, according to claim 1, wherein the reverse phase liquid chromatography is medium to low pressure liquid chromatography.

13. The method, according to claim 12, wherein the pressure is about 10 to about 200 pounds per square inch, inclusive.

14. The method, according to claim 12, wherein the pressure is about 20 to about 80 pounds per square inch.

15. The method, according to claim 1, wherein said second chromatography step is carried out on a normal phase column.

16. The method, according to claim 1, further including, prior to step (a), the step of passing the extract through a reverse phase liquid chromatography column without causing taxol and the natural analogues of taxol to be adsorbed by the adsorbent.

17. The method, according to claim 1, wherein the adsorbent is selected from the group consisting of hydrocarbon-bonded silica, cyano-bonded silica, and phenylalkyl-bonded silica.

18. The method, according to claim 17, wherein the hydrocarbon-bonded silica has $C_8$ to $C_{18}$ alkyl groups and the elutant is a 0% to 100% gradient of a water-miscible organic solvent in water.

19. The method, according to claim 18, wherein the hydrocarbon-bonded silica is $C_{18}$ bonded silica gel.

20. The method, according to claim 18, wherein the water-miscible organic solvent is acetonitrile.

21. The method, according to claim 1, wherein said ozonolysis is carried out before a second chromatography step.

22. The method, according to claim 1, wherein said ozone-reactive analogue is selected from the group consisting of cephalomannine, brevitaxane, taxane I, taxane II, taxane III, and taxane IV.

* * * * *

UNITED STATES PATENT AND TRADEMARK OFFICE
CERTIFICATE OF CORRECTION

PATENT NO. : 5,475,120
DATED : December 12, 1995
INVENTOR(S) : Koppaka V. Rao

It is certified that error appears in the above-identified patent and that said Letters Patent is hereby corrected as shown below:

Column 4: line 10: "taxaries" should read --taxanes--; line 26: "tiffs" should read --this--.

Column 5: line 9: "convened" should read --converted--; line 63: "-$C_5H_{11}$" should read -- -$C_6H_5$ --.

Column 6: line 4: "Tazxol C," should read --Taxol C,--; line 21: "Tacxol-7-xyloside," should read --Taxol-7-xyloside,--; line 58: "$R_1=AC$," should read --$R_1=Ac$,--.

Column 8: line 20: "water-chlorc, form" should read --water-chloroform--.

Column 9: line 9: "taxaries" should read --taxanes--; line 64: "pans" should read --parts--.

Column 10: lines 15-16: "(5) 10-ale-acetyl taxol" should read --(5) 10-deacetyl taxol--; line 40: "10deacetylbaccatin III," should read --10-deacetylbaccatin III,--.

Column 11: line 4: "10deacetylbaccatin III," should read --10-deacetylbaccatin III,--; line 30: "Taxus fioridana" should read --Taxus floridana--; line 32: "Taxus fioridana" should read --Taxus floridana--; line 39: "10deacetylbaccatin III," should read --10-deacetylbaccatin III,--; line 40: "10deacetylbaccatin III," should read --10-deacetylbaccatin III,--.

UNITED STATES PATENT AND TRADEMARK OFFICE
CERTIFICATE OF CORRECTION

PATENT NO. : 5,475,120
DATED : December 12, 1995
INVENTOR(S) : Koppaka V. Rao

It is certified that error appears in the above-identified patent and that said Letters Patent is hereby corrected as shown below:

Column 13: line 18: "taxaries" should read --taxanes--.

Column 14: line 39: "275 ran," should read --275 nm,--.

Column 15: line 21: "vdth" should read --with--; line 52: "the: column" should read --the column--.

Column 16: line 34: "taxaries" should read --taxanes--.

Column 17: line 24: "OH" should read --OAc--; line 45: should read --O--.

Column 19: line 29: "1716 cm$^{31}$" should read --1716 cm$^{-1}$--; lines 29-30: "(CDC11$_3$/DMSO)" should read --(CDC1$_3$/DMSO)--; line 32: "7.5(d, J=7 Hz, 3H)," should read --7.51 (d, J=7 Hz, 3H),--.

Column 20: line 11: "C, 62.88; C, 62.88; H, 6.10;" should read --C, 62.88; H, 6.10;--; line 22: "2.318 (m, 1H," should read --2.318 (m, 1H),--; line 38: "1520 cm-." should read --1520 cm$^{-1}$.--; line 55: "1520 cm-." should read --1520 cm$^{-1}$.--.

Column 21: line 38: "35°-45°C." should read --35°-45°C)--; line 55: "(fractions i35-150)" should read --(fractions 135-150)--; line 60: "phmt" should read --plant--.

Column 22: line 31: "taxaries" should read --taxanes--.

UNITED STATES PATENT AND TRADEMARK OFFICE
CERTIFICATE OF CORRECTION

PATENT NO. : 5,475,120
DATED : December 12, 1995
INVENTOR(S) : Koppaka V. Rao

It is certified that error appears in the above-identified patent and that said Letters Patent is hereby corrected as shown below:

Column 23: line 32: "taxaries" should read --taxanes--; line 59: "chmumy et al." should read --Chmurny et al.--.

Column 24: line 1: "Denis et aL" should read --Denis et al.--; Claim 1, lines 21-23: "new line, insert "(e) treating the second recovered taxol and the natural analogues of taxol by a second chromoatography step."" should read --(e) treating the recovered taxol and the natural analogues of taxol by a second chromatography step.--.

Signed and Sealed this

Thirteenth Day of July, 1999

Attest:

Q. TODD DICKINSON

Attesting Officer

Acting Commissioner of Patents and Trademarks